(12) United States Patent
Eby et al.

(10) Patent No.: US 6,670,530 B2
(45) Date of Patent: Dec. 30, 2003

(54) SOYBEAN CULTIVAR 927494

(75) Inventors: William H. Eby, Panora, IA (US); William K. Rhodes, Queenstown, MD (US)

(73) Assignees: Stine Seed Farm, Inc., Adel, IA (US); Asgrow Seed Company LLC, Ames, IA (US)

( * ) Notice: Subject to any disclaimer, the term of this patent is extended or adjusted under 35 U.S.C. 154(b) by 0 days.

(21) Appl. No.: 10/052,219

(22) Filed: Jan. 17, 2002

(65) Prior Publication Data

US 2003/0135895 A1 Jul. 17, 2003

(51) Int. Cl.$^7$ .............. A01H 5/00; A01H 5/10; A01H 1/02; C12N 5/04; C12N 15/82
(52) U.S. Cl. .............. 800/312; 800/260; 800/268; 800/279; 800/281; 800/284; 800/300; 800/301; 800/302; 435/415; 435/426; 435/430
(58) Field of Search .............. 800/312, 260, 800/266, 267, 268, 278, 279, 281, 284, 300, 301, 302; 435/415, 419, 426, 468

(56) References Cited

U.S. PATENT DOCUMENTS 6,140,558 A * 10/2000 Holmes ............ 800/312

* cited by examiner

*Primary Examiner*—Elizabeth F. McElwain
(74) *Attorney, Agent, or Firm*—Jondle & Associates PC

(57) ABSTRACT

A novel soybean cultivar, designated 927494, is disclosed. The invention relates to the seeds of soybean cultivar 927494, to the plants of soybean 927494 and to methods for producing a soybean plant produced by crossing the cultivar 927494 with itself or another soybean variety. The invention further relates to hybrid soybean seeds and plants produced by crossing the cultivar 927494 with another soybean cultivar.

18 Claims, No Drawings

US 6,670,530 B2

SOYBEAN CULTIVAR 927494

BACKGROUND OF THE INVENTION

The present invention relates to a new and distinctive soybean cultivar, designated 927494. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new soybean cultivars.

The development of new soybean cultivars requires the development and selection of soybean varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Soybean, *Glycine max* (L), is an important and valuable field crop. Thus, a continuing goal of plant breeders is to develop stable, high yielding soybean cultivars that are agronomically sound. The reasons for this goal are obviously to maximize the amount of grain produced on the land used and to supply food for both animals and humans. To accomplish this goal, the soybean breeder must select and develop soybean plants that have the traits that result in superior cultivars.

SUMMARY OF THE INVENTION

According to the invention, there is provided a novel soybean cultivar, designated 927494. This invention thus relates to the seeds of soybean cultivar 927494, to the plants of soybean 927494 and to methods for producing a soybean plant produced by crossing the soybean 927494 with itself or another soybean line, and the creation of variants by mutagenesis or transformation of soybean 927494.

Thus, any such methods using the soybean variety 927494 are part of this invention: selfing, backcrosses, hybrid production, crosses to populations, and the like. All plants produced using soybean variety 927494 as a parent are within the scope of this invention. Advantageously, the soybean variety could be used in crosses with other, different, soybean plants to produce first generation ($F_1$) soybean hybrid seeds and plants with superior characteristics.

In another aspect, the present invention provides for single or multiple gene converted plants of 927494. The transferred gene(s) may preferably be a dominant or recessive allele. Preferably, the transferred gene(s) will confer such traits as herbicide resistance, insect resistance, resistance for bacterial, fungal, or viral disease, male fertility, male sterility, enhanced nutritional quality, and industrial usage. The gene may be a naturally occurring soybean gene or a transgene introduced through genetic engineering techniques.

In another aspect, the present invention provides regenerable cells for use in tissue culture of soybean plant 927494. The tissue culture will preferably be capable of regenerating plants having the physiological and morphological characteristics of the foregoing soybean plant, and of regenerating plants having substantially the same genotype as the foregoing soybean plant. Preferably, the regenerable cells in such tissue cultures will be embryos, protoplasts, meristematic cells, callus, pollen, leaves, anthers, roots, root tips, flowers, seeds, pods or stems. Still further, the present invention provides soybean plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Allele. Allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Brown Stem Rot. This is a visual disease score from 1 to 9 comparing all genotypes in a given test. The score is based on leaf symptoms of yellowing and necrosis caused by brown stem rot. A score of 9 indicates no symptoms. Visual scores range to a score of 1 which indicates severe symptoms of leaf yellowing and necrosis.

Cotyledon. A cotyledon is a type of seed leaf. The cotyledon contains the food storage tissues of the seed.

Embryo. The embryo is the small plant contained within a mature seed.

Emergence. This score indicates the ability of the seed to emerge when planted 3" deep in sand and with a controlled temperature of 25° C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a 1 score indicates a very poor rate and percent of emergence.

Hilum. This refers to the scar left on the seed which marks the place where the seed was attached to the pod prior to the seed being harvested.

Hypocotyl. A hypocotyl is the portion of an embryo or seedling between the cotyledons and the root. Therefore, it can be considered a transition zone between shoot and root.

Iron-Deficiency Chlorosis. Plants are scored 1 to 9 based on visual observations. A score of 9 means no stunting of the plants or yellowing of the leaves and a score of 1 indicates the plants are dead or dying caused by iron-deficiency chlorosis, a score of 5 means plants have intermediate health with some leaf yellowing.

Lodging Resistance. Lodging is rated on a scale of 1 to 9. A score of 9 indicates erect plants. A score of 5 indicates plants are leaning at a 450 angle in relation to the ground and a score of 1 indicates plants are laying on the ground.

Maturity Date. Plants are considered mature when 95% of the pods have reached their mature color. The number of days are either calculated from August 31 or from the planting date.

Maturity Group. This refers to an agreed-on industry division of groups of varieties, based on zones in which they are adapted primarily according to day length or latitude. They consist of very long day length varieties (Groups 000, 00, 0), and extend to very short day length varieties (Groups VII, VIII, IX, X).

Oil or oil percent. Soybean seeds contain a considerable amount of oil. Oil is measured by NIR spectrophotometry, and is reported on an as is percentage basis.

Oleic Acid Percent. Oleic acid is one of the five most abundant fatty acids in soybean seeds. It is measured by gas chromatography and is reported as a percent of the total oil content.

Palmitic Acid Percent. Palmitic acid is one of the five most abundant fatty acids in soybean seeds. It is measured by gas chromatography and is reported as a percent of the total oil content.

Phytophthora Tolerance. Tolerance to Phytophthora root rot is rated on a scale of 1 to 9, with a score of 9 being the best or highest tolerance ranging down to a score of 1 which indicates the plants have no tolerance to Phytophthora.

Phenotypic Score. The Phenotypic Score is a visual rating of general appearance of the variety. All visual traits are considered in the score including healthiness, standability, appearance and freedom of disease. Ratings are scored from 1 being poor to 9 being excellent.

Plant Height. Plant height is taken from the top of soil to top node of the plant and is measured in inches.

Pod. This refers to the fruit of a soybean plant. It consists of the hull or shell (pericarp) and the soybean seeds.

Protein Percent. Soybean seeds contain a considerable amount of protein. Protein is generally measured by NIR spectrophotometry, and is reported on an as is percentage basis.

Pubescence. This refers to a covering of very fine hairs closely arranged on the leaves, stems and pods of the soybean plant.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Seed Protein Peroxidase Activity. Seed protein peroxidase activity is defined as a chemical taxonomic technique to separate cultivars based on the presence or absence of the peroxidase enzyme in the seed coat. There are two types of soybean cultivars, those having high peroxidase activity (dark red color) and those having low peroxidase activity (no color).

Seed Yield (Bushels/Acre). The yield in bushels/acre is the actual yield of the grain at harvest.

Seeds per Pound. Soybean seeds vary in seed size, therefore, the number of seeds required to make up one pound also varies. This affects the pounds of seed required to plant a given area, and can also impact end uses.

Shattering. The amount of pod dehiscence prior to harvest. Pod dehiscence involves seeds falling from the pods to the soil. This is a visual score from 1 to 9 comparing all genotypes within a given test. A score of 9 means pods have not opened and no seeds have fallen out. A score of 5 indicates approximately 50% of the pods have opened, with seeds falling to the ground and a score of 1 indicates 100% of the pods are opened.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

DETAILED DESCRIPTION OF THE INVENTION 927494 is a late maturity group III variety with resistance to Roundup™ herbicide conferring tolerance to glyphosate herbicides. 927494 has very high yield potential when compared to lines of similar maturity and has excellent agronomic characteristics including lodging resistance. 927494 has the Rps1k gene for resistance to many races of Phytophthora Root Rot.

Some of the criteria used to select in various generations include: seed yield, lodging resistance, emergence, disease tolerance, maturity, late season plant intactness, plant height and shattering resistance.

The cultivar has shown uniformity and stability, as described in the following variety description information. It has been self-pollinated a sufficient number of generations with careful attention to uniformity of plant type. The line has been increased with continued observation for uniformity.

Soybean cultivar 927494 has the following morphologic and other characteristics (based primarily on data collected at Adel, Iowa). VARIETY DESCRIPTION INFORMATION Seed Coat Color: Yellow
Seed Coat Luster: Dull
Hilum Color: (Mature Seed)—Black Cotyledon Color (Mature Seed): Yellow
Leaflet Shape and size: Ovate; medium
Flower Color: Purple
Pod color: Tan
Plant Pubescence Color: Tawny
Plant Habit: Indeterminate
Maturity Group: III
Relative Maturity: 3.8
Plant Lodging Score: 5
Plant height: 99 cm
Seed Content: Protein: 37.4%; Oil: 19.7%
Seed Size (G/100 seeds): 15.4
Physiological Responses: Roundup Ready™ Herbicide: Resistant
Disease Resistance: Phytophthora Rot (*Phytophthora megasperma* var. sojae): Resistant to Races 1, 2, 3, 4, 5, 6, 7, 8, 9, 10, 11, 13, 14, 15, 17, 18, 21, 22, 23, 24, and 26

This invention is also directed to methods for producing a soybean plant by crossing a first parent soybean plant with a second parent soybean plant, wherein the first or second soybean plant is the soybean plant from the line 927494. Further, both first and second parent soybean plants may be from the cultivar 927494. Therefore, any methods using the cultivar 927494 are part of this invention: selfing, backcrosses, hybrid breeding, and crosses to populations. Any plants produced using cultivar 927494 as a parent are within the scope of this invention.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device Agrobacterium-medicated transformation. Transformant plants obtained with the protoplasm of the invention are intended to be within the scope of this invention.

The cultivar 927494 is similar to 1827082. While similar to 1827082, there are numerous differences including: 927494 has the gene for resistance to the Roundup™ herbicides and 1827082 does not contain this gene. 927494 has a tan pod wall color while 1827082 has a brown pod wall color. Additionally, 927494 has the Rps1k gene for resistance to many races of Phytophthora Root Rot while 1827082 has the Rps1a gene.

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed variety or line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed soybean plants, using transformation methods as described below to incorporate transgenes into the genetic material of the soybean plant(s).

Expression Vectors for Soybean Transformation: Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990< Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol, acetyltransferase. Jefferson, R. A., Plant Mol. Biol. Rep. 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984).

Recently, in vivo methods for visualizing GUS activity that do not require destruction of plant tissue have been made available. Molecular Probes publication 2908, Imagene Green™, p. 1–4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which intitiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in soybean. Optionally, the inducible promoter is operably linked to a nucleotide sequence encoding a signal sequence which is operably linked to a gene for expression in soybean. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Mett et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters—A constitutive promoter is operably linked to a gene for expression in soybean or the constitutive promoter is operably linked to a nucleotide sequence encoding a signal sequence which is operably linked to a gene for expression in soybean.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO96/30530.

C. Tissue-specific or Tissue-preferred Promoters—A tissue-specific promoter is operably linked to a gene for expression in soybean. Optionally, the tissue-specific promoter is operably linked to a nucleotide sequence encoding a signal sequence which is operably linked to a gene for expression in soybean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen. Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3–17 (1987), Lerner et al., *Plant Physiol.* 91:124–129 (1989), Fontes et al., *Plant Cell*

3:483496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes—With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is a soybean plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology *CRC Press, Boca Raton* 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encoddes a protein kinase); Mindrinos et al., *Cell* 78:1089 (1994) (Arabidopsis RSP2 gene for resistance to *Pseudomonas syringae*).

B. A gene conferring resistance to a pest, such as soybean cyst nematode. See e.g., PCT Application WO96/30517; PCT Application WO93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δendotoxin genes can be purchased from American Type Culture Collection, Manassas, Va., for example, under ATCC Accession Nos. 40098, 67136, 31995 and 31998.

D. A lectin. See, for example, the disclose by Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US93/06487, the contents of which are hereby incorporated by reference. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor 1), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monterpene, a sesquiterpene, a steroid, hydroxamic acid, a phenylpropanoid derivative or another non-protein molecule with insecticidal activity.

K. An enzyme involved in the modification, including the ost-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4–2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.*

104:1467 (1994), who provide the nucleotide sequence of a maize calmodulin cDNA clone.

M. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

N. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaid\c virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A development-arrestive protein produced in nature by a plant. For example, Logemann et al., *Biol/Technology* 10:305 (1992), have shown that transgenic plants expressing the barley ribosome-inactivting gene have an increased resistance to fungal disease.

2. Genes That Confer Resistance to a Herbicide, for Example:

A. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy proprionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+ genes) and a benzonitrile (nitrilase gene). Przibila et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as:

A. Modified fatty acid metabolism, for example, by transforming a plant with an antisense gene of stearoyl-ACP desaturase to increase stearic acid content of the plant. See Knultzon et al., *Proc. Natl. Acad. Sci. U.S.A.* 89:2624 (1992).

B. Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Soybean Transformation—Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E.

Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. Agrobacterium-mediated Transformation—One method for introducing an expression vector into plants is based on the natural transformation system of Agrobacterium. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of Agrobacterium vector systems and methods for Agrobacterium-mediated gene transfer are provided by Gruber et al., supra, Miki et al., supra, and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to Agrobacterium-mediated transformation. A generally applicable method of plant transformation is microprojectile-mediated transformation wherein DNA is carried on the surface of microprojectiles measuring 1 to 4 $\mu$m. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992). See also U.S. Pat. No. 5,015,580 (Christou, et al.), issued May 14, 1991; U.S. Pat. No. 5,322,783 (Tomes, et al), issued Jun. 21, 1994.

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495–1505 (1992) and Spencer et al., *Plant Mol. Biol.* 24:51–61 (1994).

Following transformation of soybean target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular soybean line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture of Soybeans—When the term soybean plant is used in the context of the present invention, this also includes any single gene conversions of that variety. The term single gene converted plant as used herein refers to those soybean plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term backcrossing as used herein refers to the repeated crossing of a hybrid progeny back to the recurrent parent. The parental soybean plant which contributes the gene for the desired characteristic is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are specifically hereby incorporated by reference.

Further reproduction of the variety can occur by tissue culture and regeneration. Tissue culture of various tissues of soybeans and regeneration of plants therefrom is well know and widely published. For example, reference may be had to Komatsuda, T. et al., "Genotype X Sucrose Interactions for Somatic Embryogenesis in Soybean," *Crop Sci.* 31:333–337 (1991); Stephens, P. A., et al., "Agronomic Evaluation of Tissue-Culture-Derived Soybean Plants," *Theor. Appl. Genet.* (1991) 82:633–635; Komatsuda, T. et al., "Maturation and Germination of Somatic Embryos as Affected by Sucrose and Plant Growth Regulators in Soybeans *Glycine gracilis* Skvortz and *Glycine max* (L.) Merr." *Plant Cell, Tissue and Organ Culture,* 28:103–113 (1992); Dhir, S. et al., "Regeneration of Fertile Plants from Protoplasts of Soybean (*Glycine max* L. Merr.); Genotypic Differences in Culture Response," *Plant Cell Reports* (1992) 11:285–289; Pandey, P. et al., "Plant Regeneration from Leaf and Hypocotyl Explants of *Glycine-wightii* (W. and A.) VERDC. var. longicauda," *Japan J. Breed.* 42:1–5 (1992); and Shetty, K., et al., "Stimulation of In Vitro Shoot Organogenesis in *Glycine max* (Merrill.) by Allantoin and Amides," *Plant Science* 81:245–251 (1992); as well as U.S. Pat. No. 5,024,944 issued Jun. 18, 1991 to Collins et al., and U.S. Pat. No. 5,008,200 issued Apr. 16, 1991 to Ranch et al., the disclosures of which are hereby incorporated herein in their entirety by reference. Thus, another aspect of this invention is to provide cells which upon growth and differentiation produce soybean plants having the physiological and morphological characteristics of soybean variety 927494.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445, described certain techniques, the disclosures of which are incorporated herein by reference.

This invention also is directed to methods for producing a soybean plant by crossing a first parent soybean plant with a second parent soybean plant wherein the first or second parent soybean plant is a soybean plant of the variety 927494. Further, both first and second parent soybean plants can come from the soybean variety 927494. Thus, any such methods using the soybean variety 927494 are part of this invention: selfing, backcrosses, hybrid production, crosses to populations, and the like. All plants produced using soybean variety 927494 as a parent are within the scope of this invention, including those developed from varieties derived from soybean variety 927494. Advantageously, the soybean variety could be used in crosses with other, different, soybean plants to produce first generation ($F_1$) soybean hybrid seeds and plants with superior characteristics. The variety of the invention can also be used for transformation where exogenous genes are introduced and expressed by the variety of the invention. Genetic variants created either through traditional breeding methods using variety 927494 or through transformation of 927494 by any of a number of protocols known to those of skill in the art are intended to be within the scope of this invention.

As used herein, the term plant includes plant cells, plant protoplasts, plant cell tissue cultures from which soybean plants can be regenerated, plant calli, plant clumps, and plant cells that are intact in plants or parts of plants, such as embryos, pollen, ovules, flowers, pods, leaves, roots, root tips, anthers, and the like.

INDUSTRIAL USES

The seed of soybean variety 927494, the plant produced from the seed, the hybrid soybean plant produced from the crossing of the variety with any other soybean plant, hybrid seed, and various parts of the hybrid soybean plant can be utilized for human food, livestock feed, and as a raw material in industry.

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board and American Soybean Association Special Report 92S, May 1990). Changes in fatty acid composition for improved oxidative stability and nutrition are constantly sought after. Industrial uses of soybean oil which is subjected to further processing include ingredients for paints, plastics, fibers, detergents, cosmetics and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthy, less expensive replacement for animal protein in meats as well as dairy-type products.

As shown in Table 1, soybean cultivar 927494 yields higher than three commercial varieties with the increase over CX414CRR and P94B45 being significant at the 0.01 level of probability.

TABLES

In Table 1 that follows, the traits and characteristics of soybean cultivar 927494 are compared to several competing varieties of commercial soybeans of similar maturity. In the tables, column 1 shows the comparison number; column 2 is the year of the test; columns 3 and 4 give the number of locations and number of observations, respectively. Column 5 indicates the genotype and column 6 shows the mean yield in bushels per acre. Column 7 presents the t value and columns 8 and 9 present the critical t values at the 0.05% and 0.01% levels of significants, respectively.

TABLE 1

PAIRED COMPARISONS

| Comp # | Year | # of Loc. | # of Obs. | Genotype | Mean Yield | t Value | Critical t@.05 | Critical t@.01 |
|---|---|---|---|---|---|---|---|---|
| 1 | 2000 | 6 | 18 | 927494 | 49.1 | 1.44 | 1.74 | 2.57 |
|   |      |   |    | AG4101 | 47.1 |      |      |      |
| 2 | 2000 | 6 | 18 | 927494 | 49.1 | 2.81** | 1.74 | 2.57 |
|   |      |   |    | CX414CRR | 45.0 |      |      |      |
| 3 | 2000 | 6 | 18 | 927494 | 49.1 | 2.85** | 1.74 | 2.57 |
|   |      |   |    | P94B45 | 45.5 |      |      |      |

*Significant at .05 level of probability
**Significant at .01 level of probability

DEPOSIT INFORMATION

A deposit of the soybean seed of this invention is maintained by Stine Seed Farm, Inc., 2225 Laredo Trail, Adel, Iowa 50003. Access to this deposit will be available during the pendency of this application to persons determined by the Commissioner of Patents and Trademarks to be entitled thereto under 37 CFR 1.14 and 35 USC 122. Upon allowance of any claims in this application, all restrictions on the availability to the public of the variety will be irrevocably removed by affording access to a deposit of at least 2,500 seeds of the same variety with the American Type Culture Collection, Manassas, Va.

Although the foregoing invention has been described in some detail by way of illustration and example for purposes of clarity and understanding. However, it will be obvious that certain changes and modifications such as single gene modifications and mutations, somoclonal variants, variant individuals selected from large populations of the plants of the instant variety and the like may be practiced within the scope of the invention, as limited only by the scope of the appended claims.

What is claimed is:

1. Seed of a soybean variety designated 927494, representative seed having been deposited under ATOC Accession No. PTA-5417.

2. A soybean plant, or parts thereof, produced by growing the seed of claim 1.

3. Pollen of the plant of claim 2.

4. An ovule of the plant of claim 2.

5. A soybean plant, or parts thereof, having all of the physiological and morphological characteristics of the soybean plant of claim 2.

6. A tissue culture of regenerable cells from the plant of claim 2.

7. A tissue culture according to claim 6, the cells of the tissue culture being from a tissue selected from a group consisting of: leaves, pollen, embryos, cotyledon, hypocotyl, meristematic cells, roots, root tips, anthers, flowers, seeds, stems and pods.

8. A soybean plant regenerated from the tissue culture of claim 6, wherein the regenerated plant is capable of expressing all of the morphological and physiological characteristics of soybean cultivar 927494.

9. A soybean plant with all of the physiological and morphological characteristics of soybean variety 927494, wherein said soybean plant is produced by a tissue culture process using the soybean plant of claim 5 as the starting material for such a process.

10. A method for producing a hybrid soybean seed comprising crossing a first parent soybean plant with a second parent soybean plant and harvesting the resultant hybrid soybean seed, wherein said first parent soybean plant or said second parent soybean plant is the soybean plant of claim 2.

11. A method of producing an herbicide resistant soybean plant comprising transforming the soybean plant of claim 2 with a transgene that confers herbicide resistance.

12. An herbicide resistant soybean plant produced by the method of claim 11.

13. A method of producing an insect resistant soybean plant comprising transforming the soybean plant of claim 2 with a transgene that confers insect resistance.

14. An insect resistant soybean plant produced by the method of claim 13.

15. A method of producing a disease resistant soybean plant comprising transforming the soybean plant of claim 2 with a transgene that confers disease resistance.

16. A disease resistant soybean plant produced by the method of claim 15.

17. A method of producing a soybean plant with modified fatty acid or carbohydrate metabolism comprising transforming the soybean plant of claim 2 with one or more transgenes encoding a protein selected from the group consisting of stearyl-ACP desaturase, fructosyltransferase, levansucrase, alphaamylase, invertase and starch branching enzyme.

18. A soybean plant produced by the method of claim 17.

* * * * *